United States Patent [19]

Charnitski et al.

[11] 4,248,244

[45] Feb. 3, 1981

[54] METHOD FOR MEASURING HEART BEAT RATE AND CIRCUIT MEANS FOR SAME

[76] Inventors: Richard D. Charnitski, 25601 Adriana St., Mission Viejo, Calif. 92691; Curtis W. Morgan, P.O. Box 243, Sunset Beach, Calif. 90742

[21] Appl. No.: 27,933

[22] Filed: Apr. 6, 1979

[51] Int. Cl.³ .............................................. A61B 5/04
[52] U.S. Cl. .................................................. 128/706
[58] Field of Search ............... 128/639, 689, 690, 696, 128/698, 702, 703, 704, 706, 708, 902

[56] References Cited

U.S. PATENT DOCUMENTS

| | | | |
|---|---|---|---|
| 3,568,662 | 3/1971 | Everett et al. | 128/639 |
| 3,590,811 | 7/1971 | Harris | 128/708 |
| 3,599,628 | 8/1971 | Abbenante et al. | 128/698 |
| 3,611,164 | 10/1971 | Day | 128/704 |
| 3,717,140 | 2/1973 | Greenwood | 128/690 |
| 3,995,624 | 12/1976 | Maas | 128/708 |
| 4,129,125 | 12/1978 | Lester et al. | 128/702 |

Primary Examiner—William E. Kamm
Attorney, Agent, or Firm—Raymond L. Madsen

[57] ABSTRACT

There is disclosed a heart rate indicator having electrodes for coupling to the electrical impulses corresponding to each beat of the heart of a living subject, which electrodes are connected to an electronic circuit for producing a burst of alternating electronic signal in response to each electrical impulse produced at each heart beat. The electronic circuit in turn is connected to a detector circuit for detecting the peak amplitude of each burst of alternating signal and to produce an electrical pulse related in time thereto, the detector circuit in turn being connected to a microcomputer which measures the time between pulses and selectively converts the measured times into a number representing heart beat rate, the microcomputer being in turn connected to a display for displaying the number representing heart beat rate.

15 Claims, 8 Drawing Figures

METHOD FOR MEASURING HEART BEAT RATE AND CIRCUIT MEANS FOR SAME

The present invention relates to heart beat rate indicators and more particularly to a method and electronic circuits for detecting and processing the bio-potential signals produced at the heart beat of a living subject under conditions of physical activity and exercise.

In the field of heat beat rate indication, it has been the general practice to employ voltaic, microphonic, pressure, or strain gauge electrodes to pick up the heart beat the the cardio-vascular system of the living subject. These types of devices are described and discussed in U.S. Pat. Nos. 3,742,937; 3,450,133; 3,717,140; 4,009,708; 3,978,849; 3,807,388; and 4,058,118. Although such electrodes have served the purpose, they have not proved entirely satisfactory under all conditions of service for the reasons that considerable difficulty has been experienced in detecting heart beat biopotential signals in the presence of artifacts produced by the physical activity and motion of the living subject and difficulties encountered in separating the artifacts from the true biopotential heart beat signals. Heretofore, the only possible way of obtaining reliable indication of the biopotential voltages produced by the heart beat of a living subject has been to measure these voltages with electrodes attached to various parts of the body of the living subject while the subject is maintained in a non-active or rest condition.

Those concerned with the development of heart beat rate indicators have long recognized the need for electrode transducers and electronic processing circuits which separate the biopotential signals produced by motion of the living subject from the biopotentials produced by the heart beat of the living subject. The present invention fulfills these needs.

One of the most critical problems confronting designers of personal heart beat rate indicators has been the ability to produce reliable and accurate indication of heart beat rate while the subject is in physical motion or exercise conditions, which problem is overcome by the present invention.

The general purpose of this invention is to provide a personal heart beat rate indicator which embraces all the advantages of similarly employed heart beat rate indicators and possesses none of the aforedescribed disadvantages. To attain this, the present invention contemplates a unique combination of capacitive biopotential electrodes and electronic processing circuitry whereby the effects of electrical interference produced by the physical motion and exercise of the living subject as well as other sources of electrical interference are avoided.

An object of the present invention is the provision of capacitively coupling the biopotential voltages produced by the heart beat of a living subject into an electronic system for detecting the occurrence of each heart beat, separating each beat from other sources of electrical interference, processing the detected heat beats to obtain heart beat rate, and displaying the heart beat rate of the living subject.

Another object is to provide an electronic circuit in which a burst of alternating signal is generated in response to each heart beat impulse of a living subject.

A further object of the invention is a provision of an electronic circuit which detects the peak amplitude of a burst of alternating signal produced in response to the heart beat biopotential impulse of a living subject and rejects interfering signals of lesser magnitude.

A further object of the invention is the provision of a fixed time delay following the occurrence of the amplitude peak of the burst of alternating signal.

Still another object is to provide an indication at the end of the fixed delay that a possible heart beat indication has occurred.

Yet another object of the present invention is the provision of a microcomputer for the selection of the actual heart beat indications from indications produced by other motion artifacts and electrical interferences.

A still further object is to provide a microcomputer for converting the selected heart beat indications into a heart beat rate number for numerical display.

Other objects and many of the attendant advantages of this invention will be readily appreciated as the same becomes better understood by reference to the following detailed descriptions when considered in connection with the accompanying drawings in which like reference numerals designate like parts throughout the figures thereof and wherein.

Figure 7:
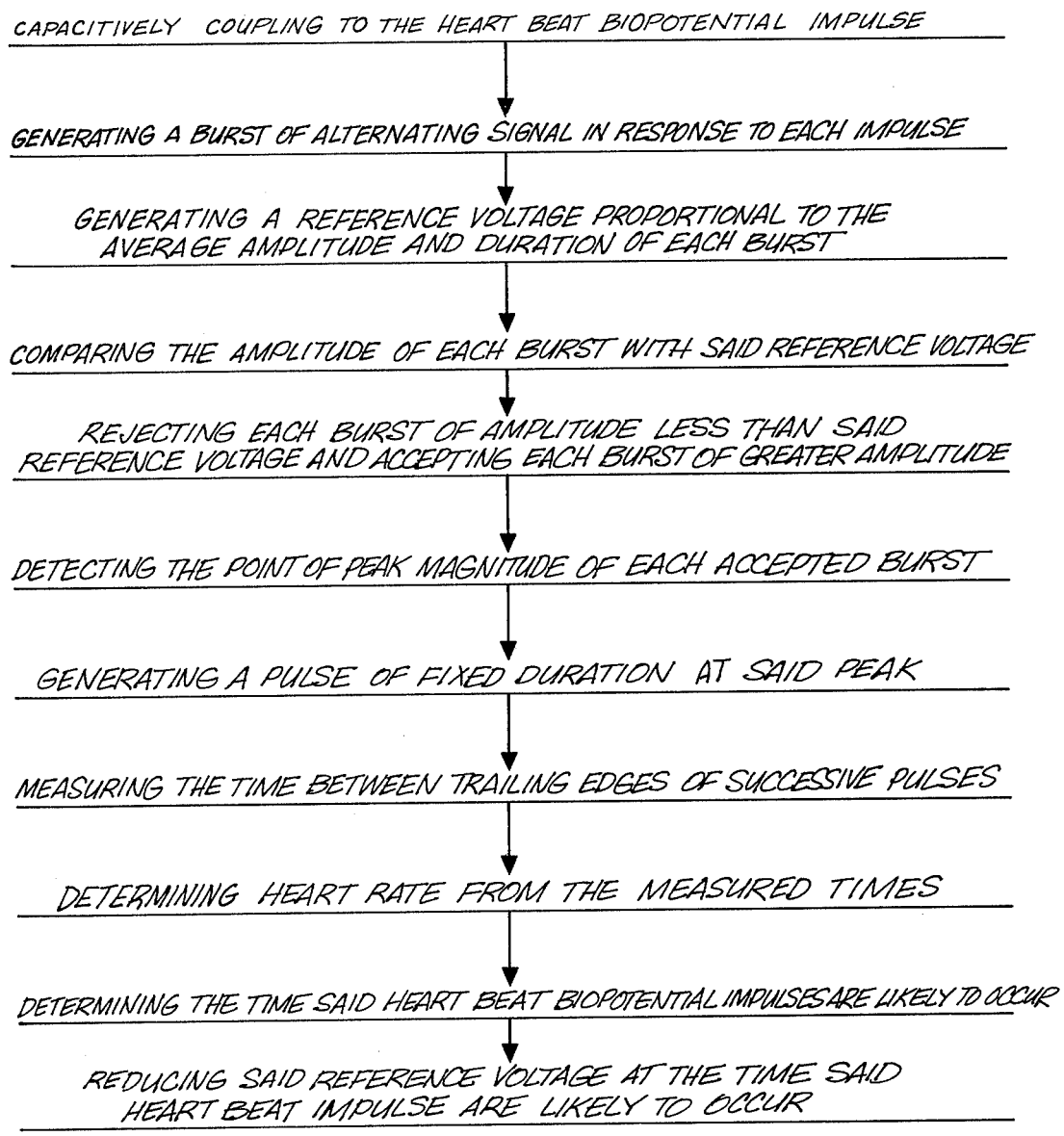
Figure 8:
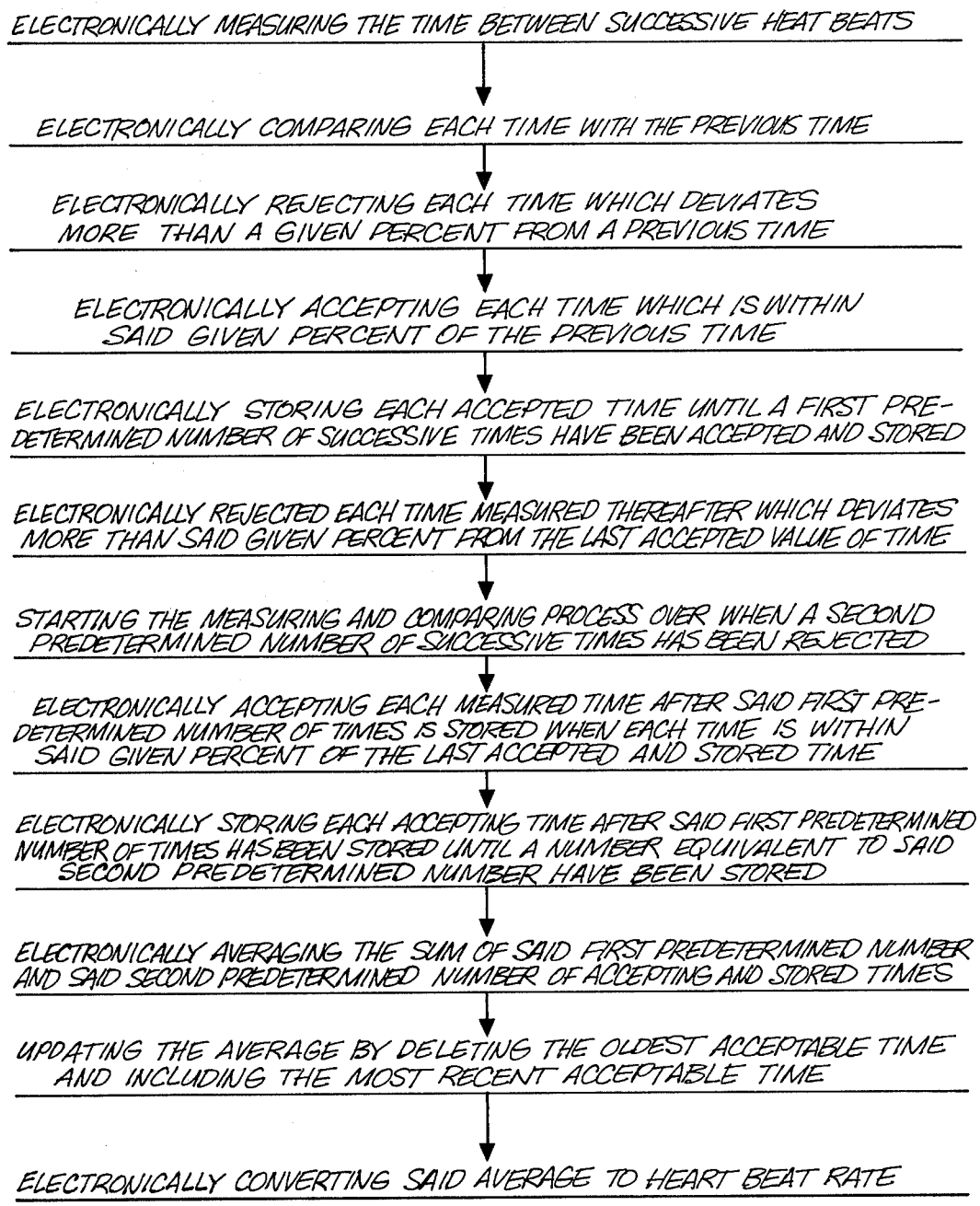

FIG. 7 describes the method of selectively detecting and indicating the heart beat rate of a living subject; and FIG. 8 describes the method of selecting heart beats from artifacts and interference and calculating the heart beat rate from the selected heart beat.

Figure 1:
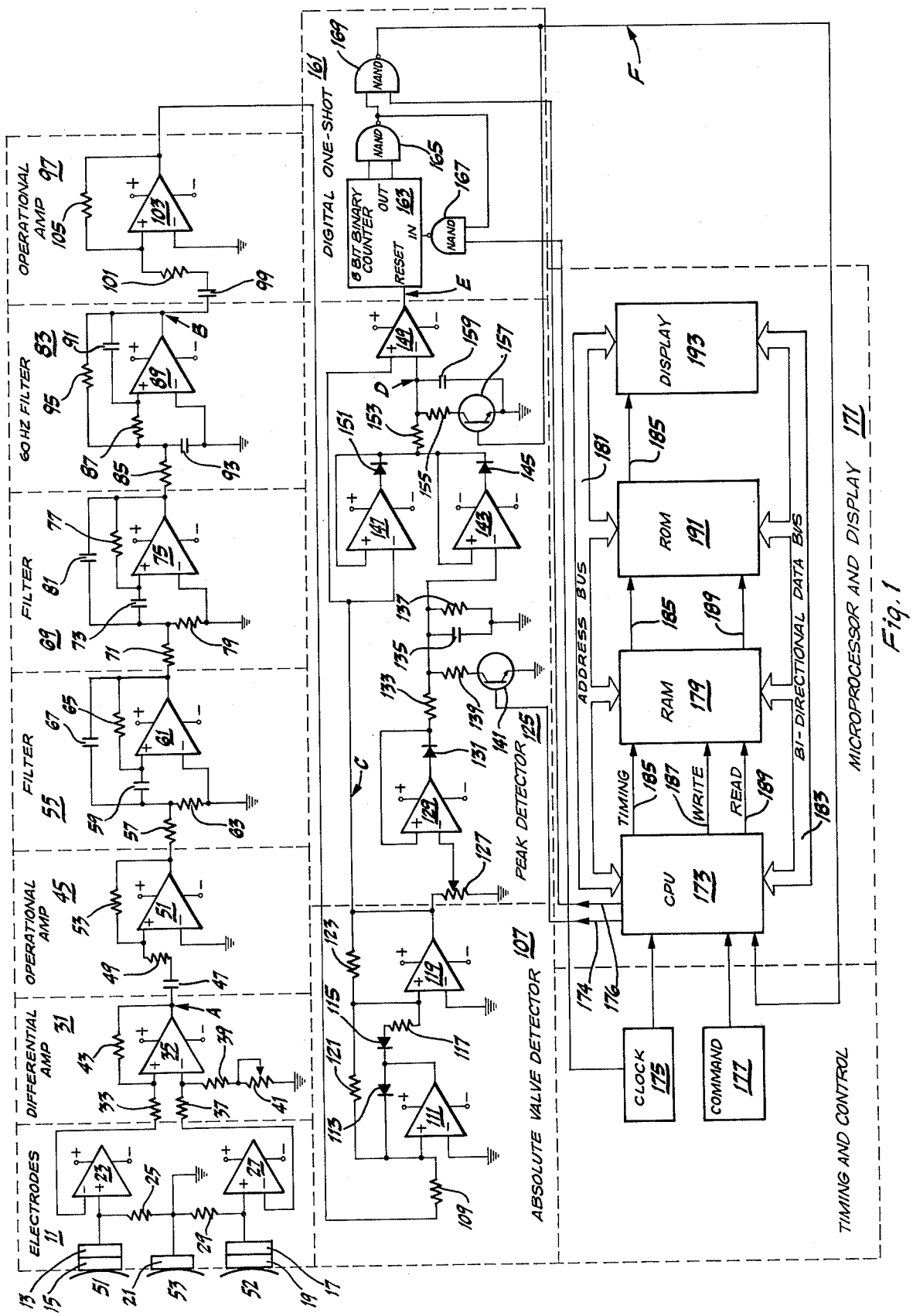
FIG. 1 shows a circuit schematic diagram, partly in block form, of a preferred circuit embodiment of the invention.

Referring now to the drawings, wherein like reference characters designate like or corresponding parts throughout the several views, there is shown in FIG. 1 (which illustrates a preferred circuit embodiment) a set of electrodes or electrode section 11 comprising a first substrate or capacitive plate 13 having a dielectric coating or covering 15 uniformly covering and attached thereto which is applied to a skin surface S1 of a living subject, a second capacitive plate or substrate 17 having a dielectric or insulative coating 19 uniformly applied thereto and in contact with a skin surface S2 of a living subject, and a reference electrode 21 which is connected to a skin surface S3 of the living subject. Capacitive plate 13 is connected to the positive input of an amplifier 23 and is also connected by a resistor 25 to reference electrode 21 and common circuit ground. The negative input of amplifier 23 is connected to the output of amplifier 23. Similarly, capacitive plate 17 is connected to the positive input of an amplifier 27 and is also connected through a resistor 29 to reference electrode 21 and common circuit ground. The negative input of amplifier 27 is connected to the output of amplifier 27.

Electrode section 11 is connected to a differential amplifier section 31 by having the output of amplifier 23 connected through a resistor 33 to the positive input of an amplifier 35 in differential amplifier section 31. Similarly, the output of amplifier 27 is connected through a resistor 37 to the negative input of amplifier 35. The negative input of amplifier 35 is connected through a resistor 39 to a variable resistor 41 which in turn is connected to common circuit ground. The positive input to amplifier 35 is connected through a resistor 43 to the output of amplifier 35.

Differential amplifier section 31 in turn is connected to a first operational amplifier section 45 by connecting the output of amplifier 35 through a capacitor 47 connected in series with a resistor 49 to the positive input of an amplifier 51 in operational amplifier section 45. The negative input of amplifier 51 is connected to common circuit ground. The positive input to amplifier 51 is further connected through a resistor 53 to the output of amplifier 51.

Operational amplifier section 45 is connected to a first filter section 55 through a resistor 57 in series with a capacitor 59 to the positive input of an amplifier 61 in filter section 55. The negative input to amplifier 61 is connected to circuit ground. A resistor 63 is connected from the junction of resistor 57 and capacitor 59 to common circuit ground. The positive input to amplifier 61 is further connected through a resistor 65 to the output of amplifier 61. A capacitor 67 is connected between the output of amplifier 61 and the junction of resistor 57 and capacitor 59.

First filter section 55 is connected to a second filter section 69 through the series combination of a resistor 71 and a capacitor 73 from the output of amplifier 61 to the positive input of an amplifier 75 of second filter section 69. The positive input of amplifier 75 is connected through a resistor 77 to the output of amplifier 75. The negative input to amplifier 75 is connected to common circuit ground. The junction of resistor 71 and capacitor 73 is connected by a resistor 79 to common circuit ground. A capacitor 81 is connected between the junction of resistor 71 and capacitor 73 to the output of amplifier 75.

Filter section 69 is connected to a 60 Hz filter section 83 through a resistor 85 connected from the output of amplifier 75 in series with a resistor 87 to the positive input of an amplifier 89 in filter section 83. The positive input to amplifier 89 is connected through a capacitor 91 to the output of amplifier 89. The negative input to amplifier 89 is connected to common circuit ground. A capacitor 93 is connected from the junction of resistor 85 and resistor 87 to common circuit ground. A resistor 95 is also connected from the junction of resistors 85 and 87 to the output of amplifier 89.

60 Hz filter section 83 is connected to a second operational amplifier section 97 through the series combination of a capacitor 99 and a resistor 101 from the output of amplifier 89 to the positive input of an amplifier 103. The negative input of amplifier 103 is connected to common circuit ground. The positive input to amplifier 103 is also connected through a resistor 105 to the output of amplifier 103.

Second operational amplifier section 97 is connected to an absolute value detector section 107 through a resistor 109 connected from the output of amplifier 103 to the positive input of an amplifier 111 in absolute value detector section 107. The negative input to amplifier 111 is connected to common circuit ground. The output of amplifier 111 is connected to the anode of a diode 113, the cathode of which is connected to the positive input of amplifier 111. The output of amplifier 111 further is connected to the cathode of a diode 115, the anode of which is connected through a resistor 117 to the positive input of an amplifier 119. The negative input of amplifier 119 is connected to common circuit ground. The positive input of amplifier 111 further is connected through a resistor 121 to the positive input of amplifier 119. The positive input of amplifier 119 also is connected through a resistor 123 to the output of amplifier 119.

Absolute value detector section 107 is connected to a peak detector section 125 through a potentiometer 127, the swinging arm of which is connected to the negative input of an amplifier 129 in peak detector section 125. The positive input to amplifier 129 is connected to the cathode of a diode 131, the anode of which is connected to the output of amplifier 129. The cathode of diode 131 also is connected through a resistor 133 to the junction of a capacitor 135 and a resistor 137 connected in parallel to common circuit ground. The junction of resistor 137 and capacitor 135 is connected through a resistor 139 to the collector of an NPN transistor 141, the emitter of which is connected to common circuit ground. The junction of resistors 133 and 137 and capacitor 135 in turn is connected to the negative input of an amplifier 143, the positive input to which is connected to the cathode of a diode 145, the anode of diode 145 being connected to the output of amplifier 143.

Absolute value detector section 107 also is connected to peak detector section 125 from the output of amplifier 119 to the negative input of an amplifier 147 and the positive input to an amplifier 149 in peak detector section 125. The positive input of amplifier 147 also is connected to the cathode of a diode 151, the anode of which is connected to the output of amplifier 147. The cathode of diode 151 further is connected through a resistor 153 to the negative input of amplifier 149. The negative input of amplifier 149 is connected through a resistor 155 to the collector of an NPN transistor 157, the emitter of which is connected to common circuit ground. A capacitor 159 also is connected from the negative input of amplifier 149 to common circuit ground.

The output of peak detector section 125 is connected to a digital one-shot multi-vibrator section 161 by connecting the output of amplifier 149 to the reset terminal of an eight bit binary counter 163 in digital one-shot section 161. The seventh and eighth bit outputs of binary counter 163 are connected to the two inputs to NAND gate 165. The output of NAND gate 165 is connected to one input of a NAND gate 167, the output of which is connected to the counting input to eight bit binary counter 163. The output of NAND gate 165 further is connected to one input of a NAND gate 169, the output of NAND gate 169 being connected to the base of transistor 157. Digital one-shot section 161 is connected to a microprocessor and display section 171 by connecting the output of NAND gate 169 to the input of a central processing unit (CPU) 173 in microprocessor and display section 171. CPU 173 has a control line 174 connected to the base of transistor 141 and a control line 176 connected to the other input of NAND gate 169. A clock 175 is connected to CPU 173 and is also connected to the other input of NAND gate 167. A command unit 177 is connected to CPU 173 for introducing the necessary control or command instructions thereto. CPU 173 is connected to a random access memory (RAM) 179 through an address bus 181, a bidirectional data bus 183, a timing connection 185, a write connection 187, and a read connection 189. CPU 173 is also connected to a read only memory (ROM) 191 by a timing connection 185, address bus 181, read connection 189, and bidirectional data bus 183. CPU is also connected through address bus 181, timing connection 185 and bidirectional data bus 183 to a display 193. ROM 191 includes a multiplicity of storage elements which are set to contain and store programs of instructions for directing the functions of microprocessor and display section 171.

Figure 2:
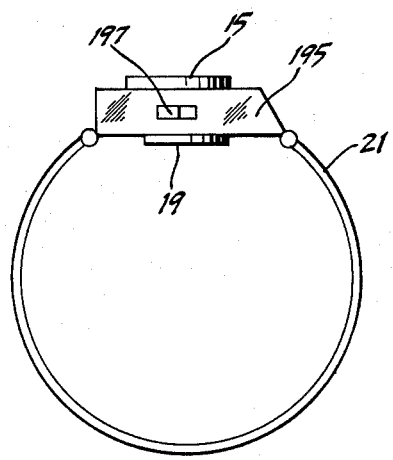
FIG. 2 illustrates a side elevation of apparatus to be worn on the wrist incorporating the circuit of FIG. 1.

FIG. 2 illustrates a side view of a packaged configuration of the invention for attaching to the wrist of a human subject. The dielectric or insulating surfaces 15 and 19 covering the conductive surfaces of capacitive plates or substrates 13 and 17 respectively are shown protruding from the top and bottom surfaces of a case member 195 to which is attached a conductive reference electrode in the form of a wrist band 21. A control switch or button 197, which may be an on-off switch or an actuating button, is shown in the side view of the device.

Figure 3:
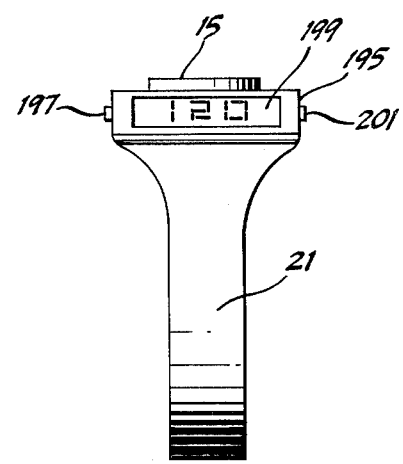
FIG. 3 shows an end view of the apparatus illustrated in FIG. 2.

FIG. 3 illustrates an end view of the device shown in FIG. 2 where a digital display 199 is shown on the side of case 195. Digital display 199 is part of display 193 of FIG. 1. Insulating or dielectric surface 15 is shown protruding from the top surface of case 195. Oppositely disposed from button or control element 197 is another button or control element 201.

Figure 4:
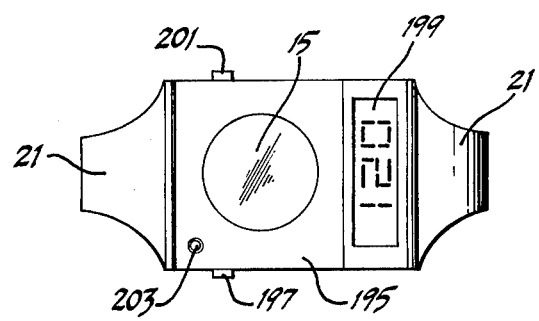
FIG. 4 shows a top view of the apparatus shown in FIGS. 2 and 3.

FIG. 4 illustrates a top view of the heart rate monitor for wrist adaptation illustrated in FIGS. 2 and 3 showing sloped digital display 199 mounted in case member 195 along with a jack element 203 which is adapted to receive a plug for an optional remote electrode connection.

Figure 5:
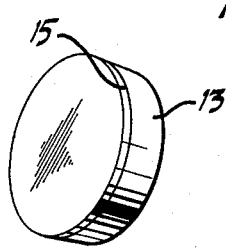
FIG. 5 shows a perspective view of the capacitive electrode element of FIGS. 1, 2, 3 and 4.

FIG. 5 illustrates a perspective view of one of the electrodes of the electrode section 11 showing a substrate or capacitive plate 13 upon which is attached or deposited a thin non porous dielectric or insulating film 15.

Figure 6:
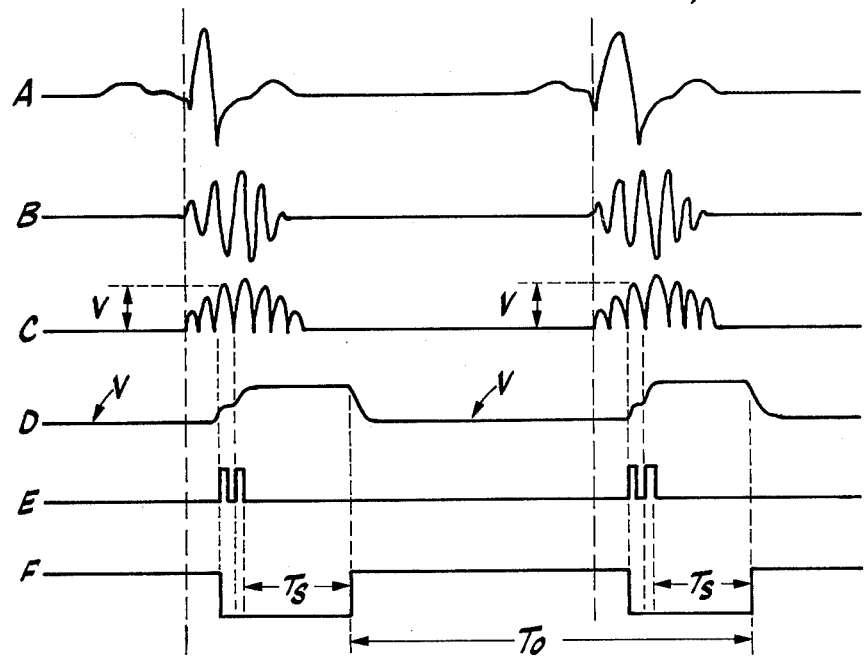
FIG. 6 illustrates a sequence of voltage wave forms at points A, B, C, D, D and F in the circuit of FIG. 1.

FIG. 6 illustrates a series of voltage wave forms designated by the letters A, B, C, D, E and F at various points in the circuit of FIG. 1. The wave form A is the typical biopotential voltage wave form which appears between the outputs of amplifiers 23 and 27. Wave form B, which is generated in response to wave form A, appears at the output of amplifier 89 with respect to circuit ground. The output of absolute value dectector section 107 at the output of amplifier 119 is indicated by wave form C. The negative input to amplifier 149 is indicated by wave form D while the positive input to amplifier 149 is indicated by wave form C. Amplifier 149 is a comparator and compares the relative amplitudes of wave forms C and D and in response produces at its output wave form E. Finally, wave form F is the output of NAND gate 169.

FIG. 7 describes the steps of the method for detecting and processing the heart beat biopotential impulses from a living subject utilized by the circuit of FIG. 1. The first step is capacitively coupling to the heart beat biopotential impulse. The next step is generating a burst of alternating signals in response to each impulse. The third step is generating a reference voltage proportional to the average amplitude and duration of each burst. The next step is comparing the amplitude of each burst with the reference voltage. The following step is rejecting each burst of amplitude less than the reference voltage and accepting each burst of greater amplitude. The next step is detecting the point of peak magnitude of each accepted burst. Next is the step of generating a pulse of fixed duration at the peak point of each accepted burst. The next succeeding step is measuring the time between trailing edges of successive pulses. The next step is calculating the heart rate from the measured times. Then, the following step is determining the time the heart beat impulses are likely to occur. Finally, the last step is reducing the reference voltage at the likely time of heart beat impulse. It should be noted that the last two steps are optional and may be eliminated from the method.

FIG. 8 illustrates the method for selecting heart beats and the heart beat rate incorporated in microprocessor and display 171 of FIG. 1. The first step is electronically measuring the time between successive burst maximum followed by the second step of electronically comparing each time with the previous time. The next step involves electronically rejecting each time which deviates more than a given percent from a previous time. The next following step is electronically accepting each time which is within said given percent of the previous time. Next, each accepted time is stored until a first predetermined number of successive times have been accepted and stored. Then the next step is electronically rejecting each time measured thereafter which deviates more than a given percent from the last accepted value of time. The next step involves starting the measuring and comparing process over when a second predetermined number of successive times have been rejected. The next step is electronically accepting each measured time, after said first predetermined number of stored times have been accepted, when each subsequent measured time is within said given percent of the last accepted and stored time. The next step is electronically storing each accepted time after said first predetermined number of stored times until a number of accepted times equivalent to said second predetermined number have been stored. Then the next step is electronically averaging the sum of said first predetermined number and said second predetermined number of accepted and stored times. The next succeeding step is updating the average by deleting the oldest acceptable time and including the most recent acceptable time. Finally, the last step is electronically converting said average to heart beat rate.

Operation of the invention may be understood by first referring to FIG. 1. Electrodes Section 11 utilizes insulated electrocardiographic electrodes as described in U.S. Pat. No. 3,882,846. However, rather than using a silicon substrate as suggested in the patent for substrates 13 and 17, an aluminum or stainless steel or other highly conductive substrate material was found to be superior in that it is not light sensitive or photovoltaic or microphonic when covered with an insulating material such as tantilum pentoxide ($Ta_2O_5$). The important requirement for the insulating covering materials 15 and 19 is that they be non-porous to avoid any skin-to-substrate electrical shorts caused by moisture penetration. The insulating coverings 15 and 19 are typically a maximum 0.001 inches in thickness. A further requirement for insulative materials 15 and 19 is that they have a high permittivity and be inert to reactions with the skin of a living subject.

Integrated with each electrode is a unity gain operational amplifier (23 and 27, respectively,) acting as an impedance transformer to reduce extraneous electrical field noise interference. These amplifiers 23 and 27 may be type LF355 field effect transistors (FET). Electrode 21 provides a direct connection to the skin surface as a ground to further reduce common mode noise input. With such a ground and one electrode on each side of the heart, a differential electrocardiograph (ECG) signal is produced between the outputs of amplifiers 23 and 27 with approximately one millivolt of peak amplitude. It is important to note that the insulated electrodes of electrode section 11 have the ability to produce an ECG signal without the necessity of preparing the skin of a living subject with a material such as a conductive gel to accept the electrodes. Moreover, since the electrodes are capacitively coupled to a living subject, very little subject motion artifacts are picked up by the electrodes, thereby reducing artifact interference.

The differential signal produced by electrode section 11 is converted to a ground referenced unipolar signal by unity gain differential amplifier section 31 having an input impedance of approximately twenty thousand ohms. The output signal of differential amplifier section 31 is illustrated as waive form A of FIG. 6. Resistor 39 and variable resistor 41 balance the inputs to amplifier 35 to obtain a high common mode interference rejection.

Operational amplifier section 45 provides a voltage gain of approximately one hundred to increase the ECG signal capacitively coupled from differential amplifier section 31 to approximately 0.1 volt in peak-to-peak magnitude. The 0.1 volt ECG signal is then directed into the tandem combination filter sections 55 and 69 which are high "Q" band pass filters centered at 22 Hz. Since the ECG wave form contains both fast and slow components, and since it is the purpose of this invention to determine heart beat rate and not be concerned with waveform, the band-pass filter sections 55 and 69 were selected to respond to and pass only the higher frequency portions attributable to the well known "R" portion of the ECG wave form. Therefore, the output of filter sections 55 and 69 will contain a burst of alternating waveform of 22 Hz frequency for every heart beat with substantially very little of the lower frequency motion artifacts which may have been picked up. The band pass is not high enough to pick up any 60 Hz ac power electrical interference. To further reject any 60 Hz electrical interference, filter section 83 is employed. Filter section 83 is a low pass filter to provide about 12 dB of additional 60 Hz rejection but still high enough to pass 22 Hz frequency bursts.

It is important to note that the combination of filter sections 55, 69 and 83 produces in effect, a burst of 22 Hz alternating voltage wave form is response to the stimulation by each ECG heart beat impulse. This waveform is illustrated as waveform B of FIG. 6. Although high "Q" band pass filters are employed to produce the waveform bursts, other electronic circuits and devices are contemplated to produce the same effect.

Operational amplifier section 97 provides additional gain to raise the magnitude of the 22 Hz burst signal to about two volts in amplitude. The output of operational amplifier section 97 is then directed into absolute value detector section 107 where a unipolar ground referenced signal is generated by essentially reversing the polarity of the negative going portions of the alternating waveform to produce a purely positive going unipolar signal of successive half cycles resembling the output of a full wave rectifier circuit but with substantially no voltage drop across the diodes. This unipolar signal is illustrated as waveform C in FIG. 6.

Peak detector section 125 generates a reference voltage across capacitor 135 which is proportional to the peak amplitude of the unipolar signal appearing at the output of absolute value detector section 107. The magnitude of this reference voltage is adjustable by potentiometer 127. Diode 131 and amplifier 129 combine to form an envelope detector to rectify waveform C to produce the reference voltage across capacitor 135. The reference voltage is applied to capacitor 159 through amplifier 143 and diode 145. Before the heart beat is detected, transistor 157 is conducting and therefore the reference voltage across capacitor 135, which also appears at the junction of diodes 145 and 151, is divided by the ratio of resistor 155 to the sum of resistors 153 and 155 to produce a reference voltage across capacitor 159 designated as "V" on waveforms C and D of FIG. 6.

Resistor 133 determines the charging rate of capacitor 135 and resistor 137 determines the discharging rate of capacitor 135. Transistor 141 discharges capacitor 135 through resistor 139 when a signal is applied to the base of transistor 141 over control line 174 from CPU 173. This enables the reference voltage to be reduced to zero or a low value at selected times such as upon initial turn on of the circuit or at selected time intervals during which the heart beat impulse is most likely to occur as determined by microprocessor and display section 171, thereby enhancing the rejection of interfering signals.

Capacitor 159 is at one input to comparator amplifier 149 while the other input to amplifier 149 is connected to the signal output of absolute value detector section 107. Therefore, for an output to be generated from amplifier 149, the absolute value signal must have an amplitude greater than the reference voltage across capacitor 159. As shown in waveform C of FIG. 6, the reference voltage "V" is selected so as to be slightly less than the peak magnitude of the half wave segments of the absolute value signal. As the wave form of C exceeds the reference voltage "V", amplifier 147 and diode 151 charge capacitor 159 through resistor 153 to the voltage represented by the peak value of that segment of the waveform C exceeding the reference voltage "V". The voltage across capacitor 159 is illustrated by waveform D of FIG. 6. Since transistor 157 is not conducting, as will be explained hereinbelow, there is no resistor across capacitor 159 to discharge it and the capacitor holds the voltage to which it is charged until transistor 157 is turned on to provide a discharge path discharging capacitor 159 through resistor 155. This occurs at the end of the pulse produced by digital one-shot section 161. Therefore, when the voltage across capacitor 159 reaches the value of the largest segment of waveform C, amplifier 149 will be prevented from producing any output pulses. Since the reference voltage "V" is adjusted so that only two half wave segments of waveform C will exceed the voltage generated across capacitor 159, the output of amplifier 149 is illustrated by the two short pulses illustrated in waveform E of FIG. 6. Waveform E is applied to the reset input of 8-bit binary counter 163 to reset the counter and start it counting again. Therefore, the second pulse of waveform E resets counter 163 so that the outputs of bits 7 and 8 will be in their low voltage state causing the output of NAND gate 165 to be in a high voltage state and the output of NAND gate 169 to be in a low voltage state as illustrated by waveform F of FIG. 6. Since the base of transistor 157 is connected to the output of NAND gate 169, transistor 157 will be in the non-conducting state and capacitor 159 will hold the voltage impressed thereacross.

While the output of NAND gate 165 is high, clock 175 provides a 2,048 Hz signal to NAND gate 167. Whenever the clock signal goes to a low voltage value, the output of NAND gate 167 rises to a high value and the transition is counted by counter 163. At count 192, both the 7th and 8th bit outputs of counter 163 go to a high voltage value causing the output of NAND gate 165 to drop to a low voltage value, which in turn causes the output of NAND gate 167 to remain in a high voltage state and cease transmitting the clock signal to the input of binary counter 163. During the period of counting of the clock signal by binary counter 163, the inputs to NAND gate 169 are both high making the output of NAND gate 169 low. If a pulse occurs at a time when a heart beat signal is not expected and resets counter 163, CPU 173 causes control line 176 to go to a low state to inhibit the output of NAND gate 169 from going to a low voltage state. Therefore, the output of NAND gate 169 will have the waveform illustrated by waveform F of FIG. 6. Although the binary counter is reset upon the first pulse of waveform E, it is reset by the second pulse and begins counting 192 counts of the 2,048 Hz clock signal for a time period designated on waveform F as $T_s$. Waveform F is applied to CPU 173 such that at the end of time period $T_s$ where the waveform rises, CPU 173 performs a counting function, counting a 512 Hz waveform signal from clock 175. This count continues over a time period designated as $T_o$ until the next rising portion of waveform F. For example, if the pulse rate is sixty beats per minute, $T_0$ will be equal to one second and CPU 173 will count 512 cycles of the output of clock 175. Once the first beat-to-beat time is counted, this count is stored in RAM 179 in a location designated by CPU 173 over address bus 181. Under the direction of ROM 191, CPU 173 counts the next beat-to-beat time and compares it to the first count to determine its percent difference. If the value is within a given percent, such as 20 percent, then the second count is accepted; if not, it is rejected. If the second count is accepted, it is stored in RAM 179 and the process continues comparing each new beat-to-beat count to the previous count to determine acceptance or rejection. If any of the first four counts are rejected, all four are discarded and the entire process starts over. If any single count is rejected after the first four are accepted, this is merely ignored and not stored in RAM 179. If four counts in a row are rejected, after the initial four are accepted, all counts are discarded and the entire process starts over again. This routine continues until 8 "legitimate" counts are accumulated in RAM 179, the first four being a continuous series of acceptances, and the second four being accumulated from those that are accepted. After these 8 "legitimate" counts are stored in RAM 179, each new count which is accepted merely replaces the oldest count stored in RAM 179. Therefore, RAM 179 always contains the most recent 8 "legitimate" counts and in this way is least affected by an occasional unwanted interference signal.

Once RAM 179 contains 8 "legitimate" counts, the averaging process takes place. All 8 counts are algebraically added together by an arithmetic logic unit (ALU) (not illustrated) contained in CPU 173 to produce a sum total. This sum is then divided under the direction of the program stored in ROM 191 to produce the average legitimate count.

Once this average count is derived, it can be converted to beats per minute by one of two methods. The first method is performed mathematically by the formula: Beats Per Minute=30,720/C where C is the average count. The second method is performed by programming ROM 191 to contain a complete table of beats per minute corresponding to all the desired or possible average count values which may be encountered; therefore, when CPU 173 computes an average count, it automatically addresses a location in ROM 191 having a beats per minute value corresponding to the average count determined by CPU 173. This latter method may result in the least storage capacity requirement of ROM 191 and is simplest to implement.

Once the beats per minute number is derived, it is converted into a format to activate digital display 193. This format is produced under the direction of a program stored in ROM 191. The display may be an alphanumeric liquid crystal display (LCD) which may be driven directly from ROM 191. A typical LCD display which may be utilized is a two-and-a-half digit, 7-bar, bipolar display. ROM 191 is further programmed to cause the display to indicate the detection of each heartbeat impulse by flashing all or a portion of the digits in response to each impulse. An additional feature included in the program of ROM 191 is to hold the heart rate display indication for a present time after contact with the electrodes is broken and to pick up where the counting left off when contact is resumed. This allows the user to make one electrode contact with one hand and the other electrode contact with a part of the body where the display cannot be readily observed and then to remove the monitor and view the heart rate indicated on the display.

Clock 175 contains a 32,768 Hz crystal oscillator and associated counter to produce sub-frequencies and may be of the type known to electronic designers as CD 4060. The microprocessor formed by CPU 173, RAM 179 and ROM 191 may be of the type designated as MC 141000 manufactured by Motorola. Amplifiers 35, 51, 61, 75, 89, 103, 111, 119, 129, 143, 147 and 149 may be of the type designated as LM 324. Counter 163 may be of the type designated as 74C93. NAND gates 165, 167 and 169 may be of the type designated as 74 CO2.

Since the heart beat rate indicator described herein is not susceptible to the artifacts produced by the motion of the living subject to which it is attached, it is particularly suited to measuring heart beat rate of a living subject while the subject is in motion such as doing exercise or under a physical activity during which the continuous monitoring of heart rate is desired. Although the particular embodiment described herein is particularly suited to human subjects, it is anticipated that the present invention may also be used for animals.

It is contemplated by the present invention that the digital microprocessor disclosed herein may be replaced by other computing and calculating devices and circuitry such as analog computing elements and circuits well known to the electronic designer.

It should be noted that ROM 191 is mask programmed to provide the following functions: beat-to-beat time count; time count comparison; time count summation and averaging; time count to beats per minute conversion; percent over or under a preset heart rate; and display or LCD drive conversion.

The heart rate monitor may be worn similar to a wristwatch as illustrated in FIGS. 2, 3 and 4. When worn on the wrist, dielectric coating of surface 19 makes contact with the skin of the wrist while electrode 21 which is embodied into a conductive wristband forms the reference code. By touching insulative surface 15 at the top of the case with a finger of the other hand, the bipotential between the wrist of the hand upon which the monitor is worn and the finger of the other hand is capacitively coupled into the input of the monitor. Display 199 which may be an LCD display, is mounted in the edge of the unit so that it may be read without requiring the subject to turn the wrist.

Other embodiments anticipated by the present invention include, but are not limited to, a hand held monitor and a monitor mounted on the handlebars of a bicycle with an electrode mounted in each handle grip.

Although only heartbeat detection and display is described herein, it is anticipated that any one or more of the well known time functions of a digital wristwatch may be incorporated into the monitoring device. Further, a preset low heart rate and preset high heart rate visual or audible alarm may be incorporated to alert the wearer when the heart rate is outside of desired preset limits. It is also anticipated that the electrode on the face may be removable and attached to the body of a living subject anywhere on the other side of the heart and connected to the monitoring module by an interconnecting transmission line. This would allow continuous heart rate monitoring while permitting freedom of motion of the arms and other body parts. As illustrated in FIG. 4, the electrode could be a plug-in type utilizing jack 203.

It should now be apparent that the present invention provides a circuit arrangement which may be employed in connection with a heart rate monitor by detecting only the desired portions of the heartbeat bipotential impulse signals and by processing the detected signals under the direction of a microcomputer program in a microprocessor so that only the desired heartbeat impulses are detected and utilized to determine a heartbeat rate.

Although particular components, etc., have been discussed in connection with a specific embodiment of a heartbeat rate indicator constructed in accordance with the teachings of the present invention, others may be utilized. Furthermore, it will be understood that although an exemplary embodiment of the present invention has been disclosed and discussed, other applications and circuit arrangements are possible and that the embodiments disclosed may be subjected to various changes, modifications and substitutions without necessarily departing from the spirit of the invention.

What is claimed is:

1. A heart rate indicator comprising:
   electrode means for producing an electrical impulse corresponding to each beat of the heart of a living subject;
   circuit means connected to said electrode means for producing a burst of alternating electrical signal in response to said electrical impulse;
   detector means connected to said circuit means for detecting the point in time the peak amplitude occurs of the envelope of each burst of alternating signal and for producing an electrical pulse in response thereto;
   computing means connected to said detector means for measuring the time between each electrical pulse produced by said detector means and converting the time measurement into a number representing heartbeat rate; and
   indicating means connected to said computing means for displaying said number representing heartbeat rate.

2. The heart rate monitor described in claim 1 where said electrode means comprises a pair of capacitor electrodes adapted to be capacitively coupled to the heartbeat biopotential voltage generated in a living subject, each of said capacitor electrodes having a conductive substrate forming the plate of a capacitor insulated from the living subject by a non-porous coating of high permittivity electrical insulative material.

3. The heart rate indicator described in claim 1 wherein said circuit means connected to said electrode means comprises a high "Q" band pass filter which produces said burst of alternating electrical signal at the center frequency of said high "Q" band pass filter when stimulated by said electrical impulse from said electrode means.

4. The heart rate monitor described in claim 1 wherein said detector means comprises:
   an absolute value detector for converting the bipolar cycles of said burst of alternating signal into successive unipolar half cycles;
   an envelope detector connected to said absolute value detector for detecting and holding the peak amplitude level of each of said successive half cycles to produce a reference voltage; and
   a comparator circuit connected to said envelope detector and said absolute value detector for comparing the amplitude of each half cycle from said absolute value detector with said reference voltage from said envelope detector and producing a pulse each time the amplitude of each half cycle exceeds the reference voltage whereby the last pulse produced indicates the occurrence of the largest amplitude of the half cycles produced by said absolute value detector.

5. The heart rate monitor described in claim 1 wherein said computing means comprises a microprocessor having a central processing unit connected to said detector, a read only memory connected to said central processing unit, and a random access memory connected to said central processing unit, said read only memory having a multiplicity of storage elements set to contain and store a program of instructions for directing said central processing unit to measure time between pulses from said detector means and to determine heartbeat rate therefrom.

6. The heart rate monitor described in claim 5 wherein said storage elements of said read only memory further are set to contain and store a program of information including a table of numbers representative of all the heartbeat rates desired to be displayed.

7. The heart rate monitor described in claim 5 further including a clock connected to said central processing unit, said clock having a high frequency wave form output which is counted by said central processing unit when said central processing unit receives a pulse from said detector means and which count is stopped and a new count started when the next pulse is received by said central processing unit from said detector, said storage elements of said read only memory further being set to contain and store a program of instructions for directing said central processing unit to store each count between detector pulses in said random access memory and to reject any count that substantially deviates more than a given percentage from the average of the stored counts and to accept any count which deviates less than the given percentage from the average of the stored counts, said storage elements of said read only memory further being set to contain and store a program of instructions to direct said central processing unit to average all of the accepted counts and to determine the heartbeat rate for display by said indicating means.

8. The heart rate monitor described in claim 5 wherein said storage elements of said read only memory further are set to contain and store a program of instructions to direct said central processing unit to store in said random access memory the first count between detector pulses and to compare the next successive count with the stored first count and to reject and start counting over if the next count is not within a given percent of the first count, said storage elements of said read only memory further being set to contain and store a program of instructions to direct said central processing unit to repeat the storing and comparing and accepting and rejecting counts until four successive counts have been accepted and stored in said random access memory, said storage elements of said read only memory further being set to contain and store a program of instructions to direct said central processing unit to reject any single count following the first four accepted counts which is not within a given percent of the first for counts and to accept and store in the random access memory the next four counts which are within a given percent of the first four counts, and to reject all counts and start over again if four counts in succession are rejected, said storage elements of said read only memory further being set to contain and store a program of instructions to direct said central processing unit to update the oldest count in said random access memory after eight counts have been stored and to average said eight counts, said storage elements of said read only memory further being set to contain and store a program of instructions to direct said central processing unit to convert said average into beats per minute for display on said indicating means.

9. The heart rate monitor described in claim 7 wherein said storage elements of said read only memory further are set to contain and store a program of instructions to direct said central processing unit to convert said average count into beats per minute.

10. The heart rate monitor described in claim 9 wherein said storage elements of said read only memory further contain and store a number equal to the sum of the number of cycles of said clock waveform output counted over a period of one minute and wherein said central processing unit is directed by said read only memory to obtain said number from said read only memory and to divide said number by said average count to compute beats per minute.

11. The heart rate monitor described in claim 7 wherein said storage elements of said read only memory further are set to contain and store a table of numbers which represent all the possible heartbeat rates desired to be displayed the locations of which in said read only memory being addressed by corresponding average counts from said central processing unit, said storage elements of said read only memory further being set to contain and store a program of instructions to direct said central processing unit to use said average count to address a location in said read only memory which stores a beats per minute heart rate number which corresponds to said average count thereby obtaining said heart rate beats per minute for display.

12. The heart rate monitor described in claim 1 wherein said indicating means comprises a three-digit alpha-numeric display.

13. A method of indicating the heartbeat rate of a living subject comprising the steps of:
capacitively coupling to the heartbeat biopotential impulse of a living subject;
generating a burst of alternating signal in response to each heartbeat impulse;
generating a reference voltage proportional to the average amplitude and duration of each burst;
comparing the amplitude of each burst with said reference voltage;
rejecting each burst of amplitude less than said reference voltage and accepting each burst of greater amplitude;
detecting the point of peak magnitude of each accepted burst;
generating a pulse at fixed duration of said peak;
measuring the time between trailing edges of successive pulses; and
determining heartbeat rate from the measured times.

14. The method of determining heartbeat rate described in claim 13 further including the steps of:
determining the time said heartbeat biopotential impulses are most likely to occur; and
reducing said reference voltage at the time said heartbeat impulses are likely to occur.

15. A method of determining the heartbeat rate of a living subject comprising the steps of:
electronically measuring the time between successive heartbeats;
electronically comparing each time with the previous time;
electronically rejecting each time which deviates more than the given percent from a previous time;
electronically accepting each time which is within said given percent of the previous time;
electronically storing each accepted time until a first predetermined number of successive times have been accepted and stored;
electronically rejecting each time measured thereafter which deviates more than said given percent from the last accepted value of time;
starting the measuring and comparing process over when a second predetermined number of successive times has been rejected;
electronically accepting each measured time after said first predetermined number of times has been stored when each time is within said given percent of the last accepted and stored time;
electronically storing each accepted time after said first predetermined number of times has been stored until a number equivalent to said second predetermined number have been stored;
electronically averaging the sum of said first predetermined number and said second predetermined number of accepted and stored times;
updating the average by deleting the oldest acceptable time and including the most recent acceptable time; and
electronically converting said average to heartbeat rate.

* * * * *